United States Patent [19]

Springer et al.

[11] Patent Number: 5,565,550
[45] Date of Patent: Oct. 15, 1996

[54] ANTIBODIES TO ICAM-2, AND FRAGMENTS THEREOF

[75] Inventors: Timothy A. Springer, Newton; Donald E. Staunton, Chestnut Hill; Michael L. Dustin, Boston, all of Mass.

[73] Assignee: Dana Farber Cancer Institute, Boston, Mass.

[21] Appl. No.: 194,564

[22] Filed: Feb. 10, 1994

Related U.S. Application Data

[60] Division of Ser. No. 89,307, Jul. 12, 1993, abandoned, which is a continuation-in-part of Ser. No. 45,963, May 4, 1987, abandoned, and a continuation-in-part of Ser. No. 115,798, Nov. 2, 1987, abandoned, Ser. No. 155,943, Feb. 16, 1988, abandoned, Ser. No. 189,815, May 3, 1988, abandoned, Ser. No. 250,446, Sep. 28, 1988, abandoned, and Ser. No. 321,238, Mar. 9, 1989, abandoned.

[51] Int. Cl.$^6$ .......................... A61K 39/395; C07K 16/18; C07K 16/28
[52] U.S. Cl. ........................ 530/391.3; 530/388.2; 530/388.22; 530/388.7; 530/377.73; 530/388.5; 530/389.6; 530/387.7
[58] Field of Search ............................ 530/388.2, 388.85, 530/389.1, 388.22, 388.7, 388.73, 389.6, 389.7, 391.1, 391.3

[56] References Cited

U.S. PATENT DOCUMENTS

| | | |
|---|---|---|
| 4,722,899 | 2/1988 | Hamaoka et al. |
| 4,748,018 | 5/1988 | Stolle et al. ............................. 424/87 |
| 5,284,931 | 2/1994 | Springer et al. ................... 530/388.22 |

OTHER PUBLICATIONS

Andersen, C. B. et al., Expression of the intercellular adhesion molecule-1 (ICAM-1) in humna renal allografts and cultured human tubular cells, *Nephrol. Dial. Transplant.* 7:147–154 (1992).

Borrebaeck, C. A. K., Strategy for the production of human monoclonal antibodies using in vitro activated B cells, *J. Immunol. Methods* 123:157–165 (1989).

Butcher, E. C., Cellular and Molecular Mechanisms That Direct Leukocyte Traffic, *Amer. J. Pathol.* 136(1):3–11 (Jan. 1990).

Charlton, B. et al., Intracellular adhesion molecule (ICAM–1) inhibition can induce tolerance in vivo, *Immunol. Cell. Biol.* 69:89–93 (1991).

Cosimi, A. B. et al., In Vivo Effects Of Monoclonal Antibody To ICAM–1 (CD54) In Nonhuman Primates With Renal Allografts, *J. Immunol.* 144(12):4604–4612 (Jun. 15, 1990).

Dreyer, W. J. et al., Neutrophil Accumulation in Ishemic Canine Myocardium: Insights Into Time Course, Distribution, and Mechanism of Localization During Early Reperfusion, *Circulation* 84(1):400–411 (Jul. 1991).

Falanga, P. B. et al., Late Treatment With anti–LFA–1 (CD11a) antibody prevents cerebral malaria in a mouse model, *Eur. J. Immunol.* 21:2259–2263 (1991).

Fisher, A. et al., Prevention Of Graft Failure By An Anti–HLFA–1 Monoclonal Antibody In HLA–Mismatched Bone–Marrow Transplantation, *Lancet* 2:1058–1061 (Nov. 8, 1986).

Flavin, T. et al., Monoclonal Antibodies Against Intercellular Adhesion Molecule 1 Prolong Cardiac Allograft Survival in Cynomolgus Monkeys, *Transplant. Proc.* 23(1):533–534 (Feb. 1991).

Kavanaugh, A. F. et al., Treatment Of Refractory Rheumatoid Arthritis With An Anti–CD54 (Intracellular Adhesion Molecule–1, ICAM–1) Monoclonal Antibody, *Abstr. Proc. Amer. Coll. Rheumatology* (1992).

Lindbom, L. et al., Rabbit Leukocyte Adhesion Molecules CD11/CD18 and Their Participation in Acute and Delayed Inflammatory Responses and Leukocyte Distribution in Vivo, *Clin. Immunol. Immunopathol.* 57:105–119 (1990).

Nortamo, P. et al., A Monoclonal Antibody To The Human Leukocyte Adhesion Molocule Intercellular Adhesion Molecule–2: Cellular Distribution and Molecular Characterization of the Antigen, *J. Immunol.* 146(8):2530–2535 (Apr. 15, 1991).

Nortamo, P. et al., The expression of human intercellular adhesion molecule–2 is refractory to inflammatory cytokines, *Eur. J. Immunol.* 21:2629–2632 (1991).

Patarroyo, M. et al., Leukocyte Adhesion to Cells: Molecular Basis, Physiological Relevance, and Abnormalities, *Scan J. Immunol.* 30:129–164 (1989).

Perez, N. et al., In vivo infusion of anti LFA–1 antibody in HLA non–identical bone marrow transplantation in children: serum concentrations and biological effects, *Bone Marrow Transp.* 4:379 (1989).

Rudinger, J., Characteristics of the amino acids as components of a peptide hormone sequence, in Parsons, J. A., ed., *Peptide Hormones*, University Park Press, Baltimore, pp. 1–7 (Jun. 1976).

Simpson, P. J. et al., Sustained Limitation of Myocardial Reperfusion Injury by a Monoclonal Antibody That Alters Leukocyte Function, *Circulation* 81(1):226–237 (Jan. 1990).

Simpson, P. J. et al., Reduction of Experimental Canine Myocardial Reperfusion Injury by a Monoclonal Anbtibody (Anti–Mol, Anti–CD11b) That Inhibits Leukocyte Adhesion, *J. Clin. Invest.* 81:624–629 (Feb. 1988).

(List continued on next page.)

*Primary Examiner*—Margaret Parr
*Assistant Examiner*—Phillip Gambel
*Attorney, Agent, or Firm*—Sterne, Kessler, Goldstein & Fox

[57] ABSTRACT

The present invention relates to intercellular adhesion molecules (ICAM-2) which are involved in the process through which lymphocytes recognize and migrate to sites of inflammation as well as attach to cellular substrates during inflammation. The invention is directed toward such molecules, screening assays for identifying such molecules and antibodies capable of binding such molecules. The invention also includes uses for adhesion molecules and for the antibodies that are capable of binding them.

4 Claims, 8 Drawing Sheets

OTHER PUBLICATIONS

Tolkoff–Rubin, N. et al., Immunosuppression With Anti–I–CAM–1 (CD54) MAB In Renal Allograft Recipients, *J. Amer. Soc. Nephrol.* 2(3):820, Abstract No. 2P (Sep. 1991).

Pigott et al., The Adhesion Molecule Facts Book, Academic Press, Harcomt Brace & Company, Publishing, New York, pp. 77–78 (1993).

Harris et al., TIBTECH, vol. 11, pp. 42–44 (1993).

Konrad, Biological Barriers to Protein Delivery, Audus et al. (Eds.) Plenum Press, New York pp. 409–437 (1993).

Dillman, Annals of Internal Medicine, vol. 111, No. 7, pp. 592–603 (1989).

Kishimoto et al., Advances In Immunology, vol. 46, pp. 149–182 (1989).

Makgoba et al., Immunol. Today. vol. 10, pp. 417–422 (1989).

Goodman, Basics & Clinical Immunology, Fudenberg et al., (Eds.), Lange Medical Publications, Los Altos, Calif., pp. 32–40 (1976).

Gaifre et al., Methods in Enzymology, vol. 73, pp. 3–47 (1981).

Rothlein et al., The Journal of Immunology, vol. 137, No. 4, pp. 1270–1274 (1986).

Makgoba et al., Eur. J. Immunol., vol. 18, pp. 637–640 (1988).

Dustin et al., The Journal of Cell Biology, vol. 107, pp. 321–331 (1988).

Dustin et al., The Journal of Immunology, vol. 137, No. 1, pp. 245–254 (1986).

Gahmberg et al., Eur. J. Biochem, vol. 195 (pp. 177–182) (1990).

Dustin et al., Cold Spring Harbor Symp Quant Biol. Liv pp. 753–765 (1989).

Seaver, Genetic Engineering News, pp. 10 and 22 (1994).

```
CTAAAGATCT CCCTCCAGGC AGCCCTTGGC TGGTCCCTGC GAGCCCGTGG                    50
AGACTGCCAG AG ATG TCC TCT TTC GGT TAC AGG ACC CTG ACT GTG GCC            98
        M   S   S   F   G   Y   R   T   L   T   V   A                  -10

CTC TTC ACC CTG ATC TGC TGT CCA GGA TCG GAT GAG AAG GTA TTC             143
 L   F   T   L   I   C   C   P   G   S   D   E   K   V   F               6

GAG GTA CAC GTG AGG CCA AAG AAG CTG GCG GTT AGC CAA AGG TCC             188
 E   V   H   V   R   P   K   K   L   A   V   S   Q   R   S              21

CTC GAG GTC AAC TGC AGC ACC ACC TGT AAC CAG CCT GAA GTG GGT             233
 L   E   V   N   C   S   T   T   C   N   Q   P   E   V   G              36

GGT CTG GAG ACC TCT CTA AAT AAG ATT CTG CTG GAC GAA CAG GCT             278
 G   L   E   T   S   L   N   K   I   L   L   D   E   Q   A              51
```

FIG. 2-1

```
CAG TGG AAA CAT TAC TTG GTC TCA AAC ATC TCC CAT GAC ACG GTC    323
 Q   W   K   H   Y   L   V   S   N   I   S   H   D   T   V     66

CTC CAA TGC CAC TTC ACC TGC TCC GGG AAG CAG GAG TCA ATG AAT    568
 L   Q   C   H   F   T   C   S   G   K   Q   E   S   M   N     81

TCC AAC GTC AGC GTG TAC CAG CCT CCA AGG CAG GTC ATC CTG ACA    413
 S   N   V   S   V   Y   Q   P   P   R   Q   V   I   L   T     96

CTG CAA CCC ACT TTG GTG GCT GTG GGC AAG TCC TTC ACC ATT GAG    458
 L   Q   P   T   L   V   A   V   G   K   S   F   T   I   E    111

TGC AGG GTG CCC ACC GTG GAG CCC CTG GAC AGC CTC ACC CTC TTC    503
 C   R   V   P   T   V   E   P   L   D   S   L   T   L   F    126
```

FIG. 2-2

| | | | | | | | | | 548 |
|---|---|---|---|---|---|---|---|---|---|
| CTG | TTC | CTG | GGC | AAT | GAG | ACT | CTG | CAC | TAT | GAG | ACC | TTC | GGG | AAG |
| L | F | L | G | N | E | T | L | H | Y | E | T | F | G | K | 141 |

| | | | | | | | | | 593 |
| GCA | GCC | CCT | GCT | CCG | CAG | GAG | GCC | ACA | TTC | AAC | AGC | ACG |
| A | A | P | A | P | Q | E | A | T | F | N | S | T | 156 |

| | | | | | | | | | 238 |
| GCT | GAC | AGA | GAG | GAT | GGC | CAC | CGC | AAC | TTC | TCC | TGC | CTG | GCT | GTG |
| A | D | R | E | D | G | H | R | N | F | S | C | L | A | V | 171 |

| | | | | | | | | | 683 |
| CTG | GAC | TTG | ATG | TCT | CGC | GGT | GGC | AAC | ATC | TTT | CAC | AAA | CAC | TCA |
| L | D | L | M | S | R | G | G | N | I | F | H | K | H | S | 186 |

| | | | | | | | | | 728 |
| GCC | CCG | AAG | ATG | TTG | GAG | ATC | TAT | GAG | CCT | GTG | TCG | GAC | AGC | CAG |
| A | P | K | M | L | E | I | Y | E | P | V | S | D | S | Q | 201 |

| | | | | | | | | | 773 |
| ATG | GTC | ATC | ATA | GTC | ACG | GTG | GTG | TCG | GTG | TTG | CTG | TCC | CTG | TTC |
| M | V | I | I | V | T | V | V | S | V | L | L | S | L | F | 216 |

```
GTG ACA TCT GTC CTG CTC TGC TTC ATC TTC GGC CAG CAC TTG CGC     818
 V   T   S   V   L   L   C   F   I   F   G   Q   H   L   R     231

CAC CAG CGG ATG GGC ACC TAC GGG GTC GGA GCG GCT TGG AGG AGG     863
 H   Q   R   M   G   T   Y   G   V   G   A   A   W   R   R     246

CTG CCC CAG GCC TTC CGG CCA TAG CAACCATGAG TGGCATGCC            907
 L   P   Q   A   F   R   P                                      253

CACACCACGG TGTCACTGGA ACTCAGTGTG ACTCCTCAGG GTTGAGGTCC           957

AGCCCTGGCT GAAGGACTGT GACAGGCAGC AGAGACTTGG GACATTGCCT          1007

TTTCTAGCCC GAATACAAAC ACCTGGACTT AAAAAAAAAA AAAAA               1052
```

FIG. 2-4

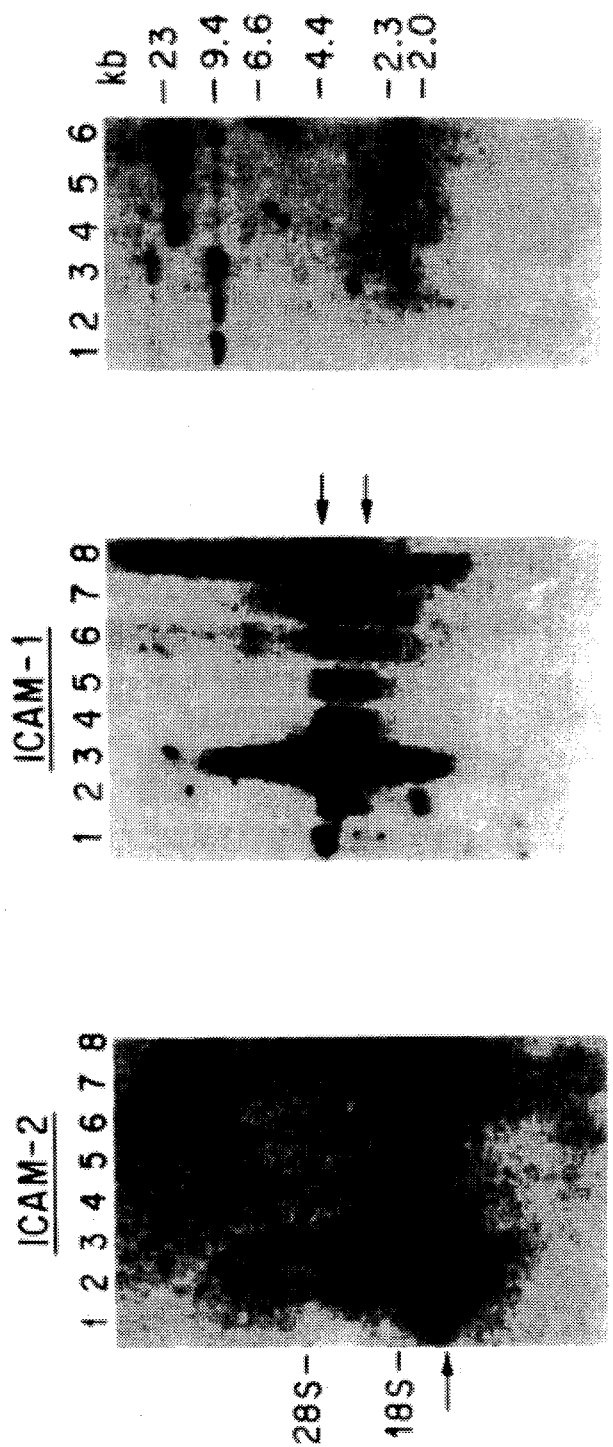

ALIGNMENT OF ICAM-2 AND AMINO TERMINAL DOMAINS OF ICAM-1

```
              D1                                       20
ICAM-2        S D E K V F E V H   V  R  P  K   L A V S Q R -  S  L E V  N

ICAM-1            Q T S V S   P   S  K   V I L P R G G  S  V L  T
                                              40
ICAM-2        C S T    C   N   Q  P E V G   G  L E T S  L  -  N  K  I L L D E Q
              C S T    C   D   Q  P K L L   G  I E T P  L  P  K  K  E L L L P G
                                      60
ICAM-2        A Q W   K   H Y L V   S  N I S H   D  T V L Q   C  H F T   C  S G K
ICAM-1        N N R   K   V Y E L   S  N V Q E   D  S Q P M   C  Y S N   C  P D G
                               80                                        100
ICAM-2        Q E S M N S N V S   V  Y  Q P P  R  Q  V  I L T L Q  P  T L V
                                                     D2
ICAM-1        Q S T A K T F L T   V  Y  W T P  E  R  V  E L A P L  P  S W Q
```

FIG. 4-1

```
ICAM-2  A V G K S F T I E C R V P T V E P L D S L T L F L F
ICAM-1  P V G K N L T L R C Q V E G G A P R A N L T V V L L
                                120

ICAM-2  R G N E T L H Y E T F G K A A P A P Q E A T A T F N
ICAM-1  R G E K E L K R E P - - - A V G E P A E V T T T V L
                    140

ICAM-2  S T A D R E D G H R N F S C L A V L D L M S R G G N
ICAM-1  V R R D H H - G A N F S C R T E L D L R P Q G L E
            160                              180        200

ICAM-2  I F H K H S A P K M L E I Y E P V S D S Q
ICAM-1  L E N T S A P Y Q L Q T F - - - - - - -
```

FIG. 4-2

ANTIBODIES TO ICAM-2, AND FRAGMENTS THEREOF

CROSS-REFERENCE TO RELATED APPLICATIONS

This application is a divisional of U.S. application Ser. No. 08/089,307, filed Jul. 12, 1993, abandoned which is pending as U.S. application Ser. No. 08/384,814, filed Feb. 6, 1995 and which is a continuation of U.S. application Ser. No. 07/454,294, filed Dec. 22, 1989, abandoned which is a continuation-in-part application of U.S. applications Ser. Nos. 07/045,963, filed May 4, 1987 (abandoned); 07/115, 798, filed Nov. 2, 1987 (abandoned); 07/155,943, filed Feb. 16, 1988 (abandoned); 07/189,815, filed May 3, 1988 (abandoned); 07/250,446, filed Sep. 28, 1988 (abandoned); and 07/321,238, filed Mar. 9, 1989 (abandoned). All of the above applications are incorporated herein by reference.

BACKGROUND OF THE INVENTION

1. Field of the Invention

The present invention relates to the intercellular adhesion molecule- 2 ("ICAM-2") which is involved in the process through which populations of lymphocytes recognize and adhere to cellular substrates so that they may migrate to sites of inflammation and interact with cells during inflammatory reactions. The present invention additionally relates to ligand molecules capable of binding to ICAM-2 intercellular adhesion molecules, and to uses for the intercellular adhesion molecule, and the ligand molecules.

2. Description of the Related Art

Leukocytes must be able to attach to cellular substrates in order to properly defend the host against foreign invaders such as bacteria or viruses. An excellent review of the defense system is provided by Eisen, H. W., (In: *Microbiology*, 3rd Ed., Harper & Row, Philadelphia, Pa. (1980), pp. 290–295 and 381–418). They must be able to attach to endothelial cells so that they can migrate from circulation to sites of ongoing inflammation. Furthermore, they must attach to antigen-presenting cells so that a normal specific immune response can occur, and finally, they must attach to appropriate target tells so that lysis of virally-infected or tumor cells can occur.

Recently, leukocyte surface molecules involved in mediating such attachments were identified using hybridoma technology. Briefly, monoclonal antibodies directed against human T-cells (Davignon, D. et al, *Proc. Natl. Acad. Sci. USA* 78:4535–4539 (1981)) and mouse spleen cells (Springer, T. et al. *Eur. J. Immunol.* 9:301–306 (1979)) were identified which bound to leukocyte surfaces and inhibited the attachment related functions described above (Springer, T. et al., *Fed. Proc.* 44:2660–2663 (1985)). The molecules identified by those antibodies were called Mac-1 and Lymphocyte Function-associated Antigen-1 (LFA-1). Mac-1 is a heterodimer found on macrophages, granulocytes and large granular lymphocytes. LFA-1 is a heterodimer found on most lymphocytes (Springer, T. A. et al. *Immunol. Rev.* 68:111–135 (1982)). These two molecules, plus a third molecule, p150,95 (which has a tissue distribution similar to Mac-1) play a role in cellular adhesion (Keizer, G. et al., *Eur. J. Immunol.* 15:1142–1147 (1985)).

The above-described leukocyte molecules were found to be members of a related family of glycoproteins (Sanchez-Madrid, F. et al., *J. Exper. Med.* 158:1785–1803 (1983); Keizer, G. D. et al., *Eur. J. Immunol.* 5:1142–1147 (1985)), termed the "CD-18 family" of glycoproteins. This glycoprotein family is composed of heterodimers having one alpha chain and one beta chain. Although the alpha chain of each of the antigens differed from one another, the beta chain was found to be highly conserved (Sanchez-Madrid, F. et al., *J. Exper. Med.* 158:1785–1803 (1983)). The beta chain of the glycoprotein family (sometimes referred to as "CD18") was found to have a molecular weight of 95 kd whereas the alpha chains were found to vary from 150 kd to 180 kd (Springer, T., *Fed. Proc.* 44:2660–2663 (1985)). Although the alpha subunits of the membrane proteins do not share the extensive homology shared by the beta subunits, close analysis of the alpha subunits of the glycoproteins has revealed that there are substantial similarities between 10 them. Reviews of the similarities between the alpha and beta subunits of the LFA-1 related glycoproteins are provided by Sanchez-Madrid, F. et al., (*J. Exper. Med.* 158:586–602 (1983); *J. Exper. Med.* 158:1785–1803 (1983)).

A group of individuals has been identified who are unable to express normal amounts of any member of this adhesion protein family on their leukocyte cell surface (Anderson, D. C. et al., *Fed. Proc.* 44:2671–2677 (1985); Anderson, D. C. et al., *J. Infect. Dis.* 52:668–689 (1985)). Lymphocytes from these patients displayed in vitro defects similar to normal counterparts whose CD-18 family of molecules had been antagonized by antibodies. Furthermore, these individuals were unable to mount a normal immune response due to an inability of their cells to adhere to cellular substrates (Anderson, D. C. et al., *Fed. Proc.* 44:2671–2677 (1985); Anderson, D. C. et al., *J. Infect. Dis.* 152:668–689 (1985)). These data show that immune reactions are mitigated when lymphocytes are unable to adhere in a normal fashion due to the lack of functional adhesion molecules of the CD-18 family.

Thus, in summary, the ability of leukocytes to maintain the health and viability of an animal requires that they be capable of adhering to other cells (such as endothelial cells). This adherence has been found to require cell-cell contacts which involve specific receptor molecules present on the cell surface of the leukocytes. These receptors enable a leukocyte to adhere to other leukocytes or to endothelial, and other non-vascular cells. The cell surface receptor molecules have been found to be highly related to one another. Humans whose leukocytes lack these cell surface receptor molecules exhibit chronic and recurring infections, as well as other clinical symptoms including defective antibody responses.

Since leukocyte adhesion is involved in the process through which foreign tissue is identified and rejected, an understanding of this process is of significant value in the fields of organ transplantation, tissue grafting, allergy and oncology.

SUMMARY OF THE INVENTION

The present invention relates to Intercellular Adhesion Molecule-2 (ICAM-2) as well as to its functional derivatives. The invention additionally pertains to antibodies and fragments of antibodies capable of inhibiting the function of ICAM-2, and to other inhibitors of ICAM-2 function. The invention additionally includes diagnostic and therapeutic uses for all of the above-described molecules.

In detail, the invention includes the intercellular adhesion molecule ICAM-2, or a functional derivative thereof, substantially free of natural contaminants.

The invention further pertains to ICAM-2 which contains at least one polypeptide selected from the group consisting of:

(a) -S-S-F-G-Y-R-T-L-T-V-A-L-;
(b) -D-E-K-V-F-E-V-H-V-R-P-K-;
(c) -G-S-L-E-V-N-C-S-T-T-C-N-;
(d) -H-Y-L-V-S-N-I-S-H-T-D-V-;
(e) -S-M-N-S-N-V-S-V-Y-Q-P-P-;
(f) -F-T-I-E-C-R-V-P-T-V-E-P-;
(g) -G-N-E-T-L-H-Y-E-T-F-G-K-;
(h) -T-A-T-F-N-S-T-A-D-R-E-D-;
(i) -H-R-N-F-S-C-L-A-V-L-D-L-;
(j) -M-V-I-I-V-T-V-V-S-V-L-L-;
(k) -S-L-F-V-T-S-V-L-L-C-F-I-; and (l) -M-G-T-Y-G-V-R-A-A-W-R-R-.

The invention also provides a recombinant or synthetic DNA molecule capable of encoding, or of expressing, ICAM-2 or a functional derivative thereof.

The invention additionally provides an antibody, and especially a monoclonal antibody, capable of binding to a molecule selected from the group consisting of ICAM-2, and a functional derivative of ICAM-2.

The invention also provides a hybridoma cell capable of producing the above-described monoclonal antibody.

The invention includes a method for producing a desired hybridoma cell that produces an antibody which is capable of binding to IISAM-2, or its functional derivative, which comprises the steps:

(a) immunizing an animal with an imunogen selected from the group consisting of: a cell expressing ICAM-2, a membrane of a cell expressing ICAM-2, ICAM-2, ICAM-2 bound to a carrier, a peptide fragment of ICAM-2, and a peptide fragment of ICAM-2 bound to a carrier, (b) fusing the spleen cells of the animal with a myeloma cell line, (c) permitting the fused spleen and myeloma cells to form antibody secreting hybridoma cells, and (d) screening the hybridoma cells for the desired hybridoma cell that is capable of producing an antibody capable of binding to ICAM-2.

The invention also provides a method for treating inflammation resulting from a response of the specific defense system in a mammalian subject which comprises providing to a subject in need of such treatment an amount of an anti-inflammatory agent sufficient to suppress the inflammation; wherein the anti-inflammatory agent is selected from the group consisting of: an antibody capable of binding to ICAM-2; a fragment of an antibody, the fragment being capable of binding to ICAM-2; ICAM-2; a functional derivative of ICAM-2; and a non-immunoglobulin antagonist of ICAM-2 other than ICAM-1, or a member of the CD-18 family of molecules.

The invention also includes a method of suppressing the metastasis of a hematopoietic tumor cell, the cell having a member of the CD-18 (especially LFA-1) for migration, which method comprises providing to a patient in need of such treatment an amount of an agent sufficient to suppress the metastasis; wherein the agent is selected from the group consisting of: an antibody capable of binding to ICAM-2; a toxin-derivatized antibody capable of binding to ICAM-2; a fragment of an antibody, the fragment being capable of binding to ICAM-2; a toxin-derivatized fragment of an antibody, the fragment being capable of binding to ICAM-2; ICAM-2; a functional derivative of ICAM-2; a toxin-derivatized ICAM-2; and a toxin-derivatized functional derivative of ICAM-2; and a non-immunoglobulin antagonist of ICAM-2 other than ICAM-1, or a member of the CD-18 family of molecules.

The invention also includes a method of suppressing the growth of an ICAM-2-expressing tumor cell which comprises providing to a patient in need of such treatment an amount of an agent sufficient to suppress the growth, wherein the agent is selected from the group consisting of: an antibody capable of binding to ICAM-2; a toxin-derivatized antibody capable of binding to ICAM-2; a fragment of an antibody, the fragment being capable of binding to ICAM-2; a toxin-derivatized fragment of an antibody, the fragment being capable of binding to ICAM-2; ICAM-2; a functional derivative of ICAM-2; a non-immunoglobulin antagonist of ICAM-2 other than ICAM-1, or a member of the CD-18 family of molecules; a toxin-derivatized member of the CD-18 family of molecules; and a toxin-derivatized functional derivative of a member of the CD-18 family of molecules.

The invention also provides a method for detecting the presence of a cell expressing ICAM-2 which comprises:

(a) incubating the cell or an extract of the cell in the presence of a nucleic acid molecule, the nucleic acid molecule being capable of hybridizing to ICAM-2 mRNA; and (b) determining whether the nucleic acid molecule has become hybridized to a complementary nucleic acid molecule present in said cell or in said extract of said cell.

The invention also provides a pharmaceutical composition comprising:

(a) an anti-inflammatory agent selected from the group consisting of: an antibody capable of binding to ICAM-2; a fragment of an antibody, the fragment being capable of binding to ICAM-2; ICAM-2; a functional derivative of ICAM-2; and a non-immunoglobulin antagonist of ICAM-2 other than ICAM-1, or a member of the CD-18 family of molecules, either alone, or in combination with (b) an immunosuppressive agent.

BRIEF DESCRIPTION OF THE FIGURES

FIGS. 1A and 1B show binding of transfected COS cells expressing ICAM-1 and ICAM-2 to LFA-1-coated plastic. FIG. A: COS cells transfected with ICAM-1 cDNA were panned on LFA-1-coated plates and the expression of ICAM-1 was analyzed by indirect immunofluorescence flow cytometry with anti-ICAM-1 monoclonal antibody RR1/1 as primary MAb. Unpanned cells (dotted line), non-adherent cells (dashed line), adherent cells (solid line). FIG. 1B: $^{51}Cr$ labelled transfected COS cells expressing ICAM-1 or ICAM-2 were bound to LFA-1-coated plastic in the presence of MAb.

FIG. 2 shows the nucleotide and amino acid sequence of ICAM-2. The amino acid sequence is numbered beginning with the first residue following the predicted cleavage site of the signal peptide. The hydrophobic putative signal peptide and transmembrane sequences (TM) are underlined. Potential N-linked glycosylation sites are boxed. The putative polyadenylation signal AATACA is overlined. Potential N-linked glycosylation sites are boxed. The putative polyadenylation signal AATACA is overlined. Both strands of the ICAM-2 cDNA were sequenced within CDM8 by sequential synthesis of complementary oligonucleotide primers and dideoxynucleotide chain termination sequencing (Sanger, F. et.al., *Proc. Natl. Acad. Sci. USA* 74:5463–5467 (1977)) according to the manufacturer's recommendations (Sequenase, U.S. Biochemical).

FIGS. 3A, 3B and 3C show the results of RNA and DNA hybridization analyses. Northern (FIGS. 3A and 3B) and Southern (FIG. 3C) blots were hybridized to the 1.1 kb $^{32}$P labeled ICAM-2 cDNA (FIGS. 3A and 3C) and rehybridized to the 3 kb $^{32}$P labeled ICAM-1 cDNA (FIG. 3B). (FIGS. 3A and 3B) 6 μg of poly(A)$^+$ RNA from the Burkitt lymphoma cell line, Ramos (lane 1), endothelial cells (lane 2), endothelial cells stimulated for three hours with LPS (lane 3), an EBV immortalized B-lymphoblastoid cell line, BBN (lane 4), epithelial carcinoma cell line, HeLa (lane 5), T lymphoma cell lines, Jurkat (lane 6) and SKW-3 (lane 7), and a promonocyte cell lines, U937 (lane 8). (C) 6 μg of genomic DNA from B cell lines BL-2 (lanes 1 and 4), ER-LCL (lanes 2 and 5) and Raji (lanes 3 and 6) digested with EcoRI (lanes 1–3) or HindIII (lanes 4–6). ICAM-2 and ICAM-1 mRNAs are indicated by arrows.

FIG. 4 shows ICAM-2 homology to ICAM-1. The entire 201 residue extracellular sequence of ICAM-2 was aligned with ICAM-1 residues 1–185 using the ALIGN program (Dayhoff, M. O. et al., *Methods Enzymol.* 91:524–545 (1983)) and by inspection. ICAM-2 residues are numbered. Identities are boxed. D1 and D2 indicate the boundary of Ig-like domains of ICAM-2 and ICAM-1. β strand predictions (Chou, P. Y. et al., *Biochemistry* 13:211–245 (1974)) of ICAM-2 are overlined and those of ICAM-1 are underlined.

DESCRIPTION OF THE PREFERRED EMBODIMENTS

Figure 1A:
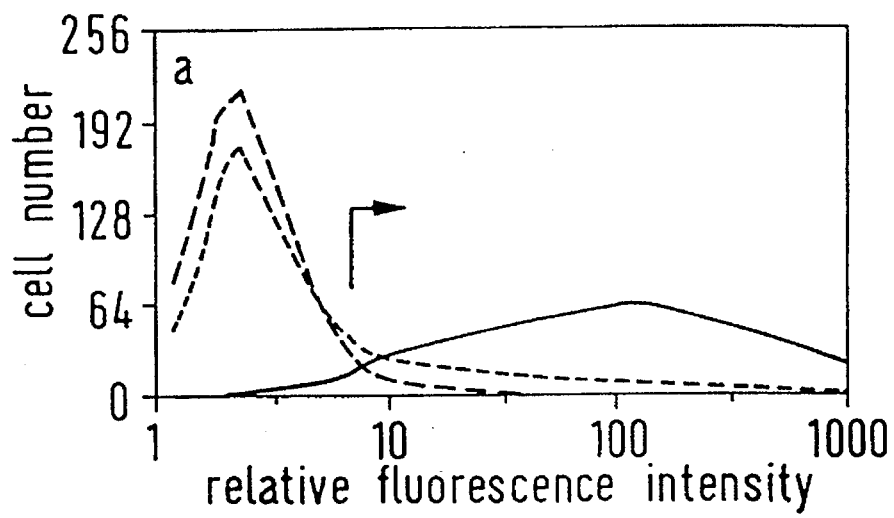

One aspect of the present invention relates to the discovery of a natural binding ligand to LFA-1. Molecules such as those of CD-18 family, which are involved in the process of cellular adhesion are referred to as "adhesion molecules."

I. LFA-1 and ICAM-1

The leukocyte adhesion molecule LFA-1 mediates a wide range of lymphocyte, monocyte, natural killer cell, and granulocyte interactions with other cells in immunity and inflammation (Springer, T. A. et al., *Ann. Rev. Immunol.* 5:223–252 (1987)).

LFA-1 is a receptor for intercellular adhesion molecule 1 (ICAM-1), a surface molecule is constitutively expressed on some tissues and induced on others in inflammation (Marlin, S. D. et al., *Cell* 51:813–819 (1987); Dustin, M. L. et al., *J. Immunol.* 137:245–254 (1986); Dustin, M. L. et al., *Immunol. Today* 9:213–215 (1988); U.S. patent application Ser. No. 07/019,440, filed Feb. 26, 1987 (abandoned) and U.S. patent application Ser. No. 07/250,446, filed Sep. 28, 1988, abandoned, both applications herein incorporated by reference).

LFA-1 functions in both antigen-specific and antigen-independent T cytotoxic, T helper, natural killer, granulocyte, and monocyte interactions with other cell types (Springer, T. A. et al., *Ann. Rev. Immunol.* 5:223–252 (1987); Kishimoto, T. K. et al., *Adv. Immunol.* (1988, in press)). LFA-1 is a leukocyte integrin, with noncovalently associated α and β glycoprotein subunits of 180 and 95 kD.

ICAM-1 is a single chain glycoprotein varying in mass on different cell types from 76–114 kD, and is a member of the Ig superfamily with five C-like domains (Dustin, M. L. et al., *Immunol. Today* 9:213–215 (1988); Staunton, D. E. et al., *Cell* 52:925–933 (1988); Simmons, D. et al., *Nature* 331:624–627 (1988)). ICAM-1 is highly inducible with cytokines including IFN-γ, TNF, and IL-1 on a wide range of cell types (Dustin, M. L. et al., *Immunol. Today* 9:213–215 (1988)). Induction of ICAM-1 on epithelial cells, endothelial cells, and fibroblasts mediates LFA-1 dependent adhesion of lymphocytes (Dustin, M. L. et al., *J. Immunol.* 137:245–254 (1986); Dustin, M. L. et al., *J. Cell. Biol.* 107:321–331 (1988); Dustin, M. L. et al., *J. Exp. Med.* 167:1323–1340 (1988)). Adhesion is blocked by pretreatment of lymphocytes with LFA-1 MAb or pretreatment of the other cell with ICAM-1 MAb (Dustin, M. L. et al., *J. Immunol,* 137:245–254 (1986); Dustin, M. L. et al., *J. Cell. Biol.* 107:321–331 (1988); Dustin, M. L. et al., *J. Exp. Med,* 167:1323–1340 (1988)). Identical results with purified ICAM-1 in artificial membranes or on Petri dishes demonstrate that LFA-1 and I CAM-1 are receptors for one another (Marlin, S. D. et al., *Cell* 51:813–819 (1987); Makgoba, M. W. et al., *Nature* 331:86–88 (1988)). For clarity, they are referred to herein as "receptor" and "ligand," respectively. Further descriptions of ICAM-1 are provided in U.S. patent applications Ser. Nos. 07/045,963, filed May 4, 1987 (abandoned); 07/115,798, filed Nov. 2, 1987 (abandoned); 07/155,943, filed Feb. 16, 1988 (abandoned); 07/189,815, filed May 3, 1988 (abandoned) or 07/250,446, filed Sep. 28, 1988 (abandoned), all of which applications are herein incorporated by reference in their entirety

II. ICAM-2

A second LFA-1 ligand, distinct from ICAM-1, has been postulated (Rothlein, R. et al., *J. Immunol.* 137:1270–1274 (1986); Makgoba, M. W. et al., *Eur. J. Immunol,* 18:637–640 (1988); Dustin, M. L. et al., *J. Cell. Biol.* 107:321–331 (1988)). The present invention concerns this second ligand, designated "ICAM-2"(for "Intercellular Adhesion Molecule-2").

ICAM-2 differs from ICAM-1 in cell distribution and in a lack of cytokine induction. ICAM-2 is an integral membrane protein with 2 Ig-like domains, whereas ICAM-1 has 5 Ig-like domains (Staunton, D. E. et al., *Cell* 52:925–933 (1988); Simmons, D. et al., *Nature* 331:624–627 (1988)). Remarkably, ICAM-2 is much more closely related to the two most N-terminal domains of ICAM-1 (34% identity) than either ICAM-1 or ICAM-2 is to other members of the Ig superfamily, demonstrating a subfamily of Ig-like ligands which bind the same integrin family receptor.

III. cDNA CLONING OF ICAM-2

Any of a variety of procedures may be used to clone the ICAM-2 gene. One such method entails analyzing a shuttle vector library of cDNA inserts (derived from an ICAM-2 expressing cell) for the presence of an insert which contains the ICAM-2 gene. Such an analysis may be conducted by transfecting cells with the vector and then assaying for ICAM-2 expression.

ICAM-2 cDNA is preferably identified when a novel modification of the procedure of Aruffo and Seed (Seed, B. et al., *Proc. Natl. Acad. Sci. USA* 84:3365–3369 (1987)) is employed for identifying ligands of adhesion molecules. In this method, a cDNA library is prepared from cells which express ICAM-2 (such as endothelial cells or Ramos, BBN B lymphoblastoid, U937 monocytic, or SKW3 lymphoblastoid, cell lines). Preferably, the cDNA library is prepared from endothelial cells. This library is used to transfect cells which do not normally express ICAM-2 (such as COS cells). The transfected cells are introduced into a petri dish which has been previously coated with LFA-1. COS cells which have been transfected with either ICAM-1 or ICAM-2 encoding sequences, and which express either of these ligands on their cell surfaces will adhere to the LFA-1 on the surface of the petri dish. Non-adherant cells are washed away, and the adherent cells are then removed from the petri dish and cultured. The recombinant ICAM-1 or ICAM-2 expressing sequences in these cells is then removed, and sequenced to determine whether it encodes ICAM-1 or ICAM-2.

In a preferred embodiment of the above-described method, anti-ICAM-1 antibody is added to the petri dish in order to prevent the adherence of ICAM-1 expressing cells. Binding of ICAM-2 transfected COS cells to LFA-1 is inhibited by EDTA and anti-LFA-1 monoclonal antibody ("MAb"), but is not inhibited by anti-ICAM-1MAb. Thus, in this embodiment, the ICAM-1 expressing cells are unable to adhere to the petri dish through ICAM-1 and are therefore mostly washed away with all of the other non-adherent cells. As a result, only cells expressing ICAM-2 are able to adhere to the petri dish.

Thus, cDNA clones are screened by expression in COS cells, and by panning for ligand-bearing COS cells using functionally-active, purified LFA-1 which has been previously bound to plastic Petri dishes. After panning, nonadherent cells are depleted of ICAM-2$^+$ cells, whereas adherent cells, released from LFA-1-coated plastic by EDTA, are almost completely ICAM-2$^+$. Adherence of ICAM-1$^+$ cells to LFA-1-coated plastic may be inhibited with RR1/1 anti-ICAM-1MAb.

Thus, in accordance with this method for cloning cDNA for ICAM-2, a cDNA library is prepared from endothelial cells, which demonstrate both the ICAM-1-dependent and ICAM-1-independent components of LFA-1-dependent adhesion (Dustin, M. L. et al., *J. Cell. Biol.* 107:321–331 (1988)) using a suitable plasmid, such as the plasmid vector CDM8. Transfected COS cells are incubated in LFA-1-coated petri dishes with anti-ICAM-1 MAb present to reduce the probability of isolating ICAM-1 cDNA's. Adherent cells are eluted with EDTA and plasmids are isolated and amplified in *E. coli*. After approximately three cycles of transfection, adherence, and plasmid isolation and one size fractionation, plasmids may be analyzed by restriction endonuclease digestion. Approximately ⅓ of plasmids having inserts greater than 1.0 kb, when introduced into COS cells by transfection, yielded adherence to LFA-1.

Alternatively, a cDNA clone of ICAM-2 can be obtained by using the genetic code (Watson, J. D., In: *Molecular Biology of the Gene,* 3rd Ed., W. A. Benjamin, Inc., Menlo Park, Calif. (1977 ), pp. 356–357) to determine the sequence of a polynucleotide capable of encoding the ICAM-2 protein.

A clone of the ICAM-2 cDNA can also be obtained by identifying the amino acid sequences of peptide fragments of the ICAM-2 protein, and then using the genetic code to construct oligonucleotide probe molecules capable of encoding the ICAM-2 peptide. The probes are then used to detect (via hybridization) those members of a cDNA library (prepared from cDNA of ICAM-2 expressing cells) which encode the ICAM-2 protein.

Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor gene (Walter, P. et al., *Proc. Natl. Acad. Sci. USA* 82:7889–7893 (1985)), tissue-type plasminogen activator (Pennica, D. et al., *Nature* 301:214–221 (1983)) and human term placental alkaline phosphatase complementary DNA (Kam, W. et al., *Proc. Natl. Acad. Sci. USA* 82:8715–8719 (1985)).

In yet another alternative way of cloning the ICAM-2 gene, a library of expression vectors is prepared by cloning DNA or, more preferably cDNA, from a cell capable of expressing ICAM-2 into an expression vector. The library is then screened for members capable of expressing a protein which binds to anti-ICAM-2 antibody, and which has a nucleotide sequence that is capable of encoding polypeptides that have the same amino acid sequence as ICAM-2 or fragments of ICAM-2.

The cloned ICAM-2 gene, obtained through the use of any of the methods described above, may be operably linked to an expression vector, and introduced into bacterial, or eukaryotic cells to produce ICAM-2 protein. Techniques for such manipulations are disclosed by Maniatis, T. et al., supra, and are well known in the art.

IV. THE AGENTS OF THE PRESENT INVENTION: ICAM-2 AND ITS FUNCTIONAL DERIVATIVES, AGONISTS AND ANTAGONISTS

The present invention is directed toward ICAM-2, its "functional derivatives," and its "agonists" and "antagonists."

A. Functional Derivatives of ICAM-2

A "functional derivative" of ICAM-2 is a compound which possesses a biological activity (either functional or structural) that is substantially similar to a biological activity of ICAM-2. The term "functional derivatives" is intended to include the "fragments," "variants," "analogs," or "chemical derivatives" of a molecule.

A "fragment" of a molecule such as ICAM-2, is meant to refer to any polypeptide subset of the molecule. Fragments of ICAM-2 which have ICAM-2 activity and which are soluble (i.e not membrane bound) are especially preferred.

A "variant" of a molecule such as ICAM-2 is meant to refer to a molecule substantially similar in structure and function to either the entire molecule, or to a fragment thereof.

An "analog" of a molecule such as ICAM-2 is meant to refer to a molecule substantially similar in function to either the entire molecule or to a fragment thereof.

A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980).

"Toxin-derivatized" molecules constitute a special class of "chemical derivatives." A "toxin-derivatized" molecule is a molecule (such as ICAM-2 or an antibody) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the cholera toxin, the diphtheria toxin, radioisotopic toxins, membrane-channel-forming toxins, etc. Procedures for coupling such moieties to a molecule are well known in the art.

Functional derivatives of ICAM-2 having up to about 100 residues may be conveniently prepared by in vitro synthesis. If desired, such fragments may be modified by reacting targeted amino acid residues of the purified or crude protein with an organic derivatizing agent that is capable of reacting with selected side chains or terminal residues. The resulting covalent derivatives may be used to identify residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking an ICAM-2 functional derivative molecule to a water-insoluble support matrix or surface for use in the method for cleaving an ICAM-2 functional derivatives fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, Proteins: *Structure and Molecule Properties,* W. H. Freeman & Co., San Francisco, pp. 79–86 (1983)), acetylation of the N-terminal amine, and, in some instances, amidation of the C-terminal carboxyl groups.

Functional derivatives of ICAM-2 having altered amino acid sequences can also be prepared by mutations in the DNA. The nucleotide sequence which encodes the ICAM-2 gene is shown in FIG. 2. Such variants include, for example, deletions from, or insertions or substitutions of, residues within the amino acid sequence shown in FIG. 2. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these functional derivatives ordinarily are prepared by site-directed mutagenesis of nucleotides in the DNA encoding the ICAM-2 molecule, thereby producing DNA encoding the functional derivative, and thereafter expressing the DNA in recombinant cell culture. The functional derivatives typically exhibit the same qualitative biological activity as the naturally occurring analog. They may, however, differ substantially in such characteristics with respect to the normally produced ICAM-2 molecule.

While the site for introducing an amino acid sequence variation is predetermined, the mutation per se need not be predetermined. For example, to optimize the performance of a mutation at a given site, random mutagenesis may be conducted at the target codon or region and the expressed ICAM-2 functional derivatives screened for the optimal combination of desired activity. Techniques for making substitution mutations at predetermined sites in DNA having a known sequence are well known, for example, site-specific mutagenesis.

Preparation of an ICAM-2 functional derivative molecule in accordance herewith is preferably achieved by site-specific mutagenesis of DNA that encodes an earlier prepared functional derivatives or a nonvariant version of the protein. Site-specific mutagenesis allows the production of ICAM-2 functional derivatives through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as JM101 cells, and clones are selected that include recombinant vectors bearing the mutated sequence arrangement.

After such a Clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous. Deletions may also comprise an immunoglobulin domain, such as domains 1 or 2 of ICAM-2. Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete ICAM-2 molecule sequence) may range generally from about 1 to 10 residues, more preferably 1 to 5. An example of a terminal insertion includes a fusion of a signal sequence, whether heterologous or homologous to the host cell, to the N-terminus of the molecule to facilitate the secretion of the ICAM-2 functional derivative from recombinant hosts.

The third group of functional derivatives are those in which at least one amino acid residue in the ICAM-2 molecule, and preferably, only one, has been removed and a different residue inserted in its place. Such substitutions preferably are made in accordance with the following Table when it is desired to modulate finely the characteristics of the ICAM-2 molecule.

TABLE 1

| Original Residue | Exemplary Substitutions |
| --- | --- |
| Ala | gly; ser |
| Arg | lys |
| Asn | gln; his |
| Asp | glu |
| cys | ser |
| Gln | asn |

TABLE 1-continued

| Original Residue | Exemplary Substitutions |
| --- | --- |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the ICAM-2 molecule. However, when it is difficult to predict the exact effect of the substitution, deletion, or insertion in advance of doing so, one skilled in the art will appreciate that the effect will be evaluated by routine screening assays. For example, a functional derivative typically is made by site-specific mutagenesis of the native ICAM-2 molecule-encoding nucleic acid, expression of the variant nucleic acid in recombinant cell culture, and, optionally, purification from the cell culture, for example, by immunoaffinity adsorption on an anti-ICAM-2 molecule antibody column (to absorb the functional derivative by binding it to at least one remaining immune epitope).

Mutations designed to increase the affinity of ICAM-2 may be guided by the introduction of the amino acid residues which are present at homologous positions in ICAM-1. Similarly, such mutant ICAM-2 molecules may be prepared which lack N-linked CHO at homologous positions in ICAM-1.

The activity of the cell lysate or purified ICAM-1 molecule functional derivative is then screened in a suitable screening assay for the desired characteristic. For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

B. Agonists and Antagonists of ICAM-2

An "agonist" of ICAM-2 is a compound which enhances or increases the ability of ICAM-2 to carry out any of its biological functions. An example of such an agonist is an agent which increases the ability of ICAM-2 to bind to a cellular receptor or..viral protein.

An "antagonist" of ICAM-2 is a compound which diminishes or prevents the ability of ICAM-2 to carry out any of its biological functions. Examples of such antagonists include ICAM-1, functional derivatives of ICAM-1, anti-ICAM-2 antibody, anti-LFA-1 antibody, etc.

The cellular aggregation assays described in U.S. patent applications Ser. Nos. 07/045,963, filed May 4, 1987 (abandoned); 07/115,798, filed Nov. 2, 1987 (abandoned); 07/155, 943, filed Feb. 16, 1988 (abandoned); 07/189,815, filed May 3, 1988 (abandoned) or 07/250,446, filed Sep. 28, 1988 (abandoned), all of which applications have been herein incorporated by reference in their entirety, are capable of measuring LFA-1 dependent aggregation, and may be employed to identify agents which affect the extent of ICAM-2/LFA-1 aggregation. Thus, such assays may be employed to identify agonists and antagonists of ICAM-2. Antagonists may act by impairing the ability of IFA-1 or of ICAM-2 to mediate aggregation. Additionally, non-immunoglobulin (i.e., chemical) agents may be examined, using the above-described assay, to determine whether they are agonists or antagonists of ICAM-2/LFA-1 aggregation.

C. Anti-ICAM-2 Antibody

The preferred immunoglobulin antagonist of the present invention is an antibody to ICAM-2. Suitable antibodies can be obtained in any of a variety of ways.

An antigenic molecule such as ICAM-2 are naturally expressed on the surfaces of lymphocytes. Thus, the introduction of such cells into an appropriate animal, as by intraperitoneal injection, etc., will result in the production of antibodies capable of binding to ICAM-2 or members of the CD-18 family of molecules. If desired, the serum of such an animal may be removed and used as a source of polyclonal antibodies capable of binding these molecules.

Alternatively, anti-ICAM-2 antibodies may be produced by adaptation of the method of Selden, R. F. (European Patent Application Publication No. 289,034) or Selden R. F. et al. (*Science* 236:714–718 (1987)). In accordance with such an adaptation of this method, the cells of a suitable animal (i.e. such as, for example, a mouse, etc.) are transfected with a vector capable of expressing either the intact ICAM-2 molecule, or a fragment of ICAM-2. The production of ICAM-2 in the transfected cells of the animal will elicit an immune response in the animal, and lead to the production of anti-ICAM-2 antibodies by the animal.

Alternatively, anti-ICAM-2 antibodies may be made by introducing ICAM-2, or peptide fragments thereof, into an appropriate animal. The immunized animal will produce polyclonal antibody in response to such exposure. The use of peptide fragments of ICAM-2 permits one to obtain region specific antibodies which are reactive only with the epitope(s) contained in the peptide fragments used to immunize the animals.

It is, however, preferable to remove splenocytes from animals (immunized in either of the ways described above), to fuse such spleen cells with a myeloma cell line and to permit such fusion cells to form a hybridoma cell which secretes monoclonal antibodies capable of binding ICAM-2.

The hybridoma cells, obtained in the manner described above may be screened by a variety of methods to identify desired hybridoma cells that secrete antibody capable of binding to ICAM-2. In a preferred screening assay, such molecules are identified by their ability to inhibit the aggregation of ICAM-2-expressing, ICAM-1-non-expressing cells. Antibodies capable of inhibiting such aggregation are then further screened to determine whether they inhibit such aggregation by binding to ICAM-2, or to a member of the CD-18 family of molecules. Any means capable of distinguishing ICAM-2 from the CD-18 family of molecules may be employed in such a screen. Thus, for example, the antigen bound by the antibody may be analyzed as by immunoprecipitation and polyacrylamide gel electrophoresis. It is possible to distinguish between those antibodies which bind to members of the CD-18 family of molecules from those which bind ICAM-2 by screening for the ability of the antibody to bind to cells which express LFA-1, but not ICAM-2 (or vice versa). The ability of an antibody to bind to a cell expressing LFA-1 but not ICAM-2 may be detected by means commonly employed by those of ordinary skill. Such means include immunoassays (especially those using immunoflorescence), cellular agglutination, filter binding studies, antibody precipitation, etc.

In addition to the above-described functional derivatives of ICAM-2, other agents which may be used in accordance of the present invention in the treatment of vital infection or inflammation include antibody to ICAM-2, anti-idiotypic antibodies to anti-ICAM-2 antibodies, and receptor molecules, or fragments of such molecules, which are capable of binding to ICAM-2.

The antibodies to ICAM-2 (or functional derivatives of ICAM-2) which may be employed may be either polyclonal or monoclonal.

The anti-idiotypic antibodies of interest to the present invention are capable of binding in competition with (or to the exclusion of) ICAM-2. Such antibodies can be obtained, for example, by raising antibody to an anti-ICAM-2 antibody, and then screening the antibody for the ability to bind a natural binding ligand of ICAM-2.

Since molecules of the CD-18 family are able to bind to ICAM-2, administration of such molecules (for example as heterodimers having both alpha and beta subunits, or as molecules composed of only an alpha, or a beta subunit, or as molecules having fragments of either or both subunits) is able to compete with (or exclude) HRV for binding to ICAM-21 present on cells.

The anti-aggregation antibodies of the present invention may be identified and titered in any of a variety of ways. For example, one can measure the ability of the antibodies to differentially bind to cells which express ICAM-2 (such as activated endothelial cells), and their inability to bind to cells which fail to express ICAM-2. Suitable assays of cellular aggregation are those described in U.S. patent applications Ser. Nos. 07/045,963, filed May 4, 1987 (abandoned); 07/115,798, filed Nov. 2, 1987 (abandoned); 07/155, 943, filed Feb. 16, 1988 (abandoned); 07/189,815, filed May 3, 1988 (abandoned) or 07/250,446, filed Sep. 28, 1988 (abandoned), all of which applications have been herein incorporated by reference in their entirety. Alternatively, the capacity of the antibodies to bind to ICAM-2 or to peptide fragments of ICAM-2 can be measured. As will be readily appreciated by those of ordinary skill, the above assays may be modified, or performed in a different sequential order to provide a variety of potential screening assays, each of which is capable of identifying and discriminating between antibodies capable of binding to ICAM-1 versus members of the CD-18 family of molecules.

In a more preferred method, antibody can be selected for its ability to bind to COS cells expressing ICAM-2, but not to COS cells which do not express ICAM-2.

D. Preparation of the Agents of the Present Invention

The agents of the present invention may be obtained by natural processes (such as, for example, by inducing an animal, plant, fungi, bacteria, etc., to produce a non-immunoglobulin antagonist of ICAM-2, or by inducing an animal to produce polyclonal antibodies capable of binding to ICAM-2); by synthetic methods (such as, for example, by using the Merrifield method for synthesizing polypeptides to synthesize ICAM-2, functional derivatives of ICAM-2, or protein antagonists of ICAM-2 (either immunoglobulin or non-immunoglobulin)); by hybridoma technology (such as, for example, to produce monoclonal antibodies capable of binding to ICAM-2); or by recombinant technology (such as, for example, to produce the agents of the present invention in diverse hosts (i.e., yeast, bacteria, fungi, cultured mammalian cells, etc.), or from recombinant plasmids or viral vectors). The choice of which method to employ will depend upon factors such as convenience, desired yield, etc. It is not necessary to employ only one of the above-described methods, processes, or technologies to produce a particular anti-inflammatory agent; the above-described processes, methods, and technologies may be combined in order to obtain a particular agent.

V. USES OF ICAM-2, AND ITS FUNCTIONAL DERIVATIVES, AGONISTS AND ANTAGONISTS

A. Suppression of Inflammation

One aspect of the present invention derives from the ability of ICAM-2 and its functional derivatives to interact with receptors of the CD-18 family of molecules, especially LFA-1 or with vital proteins (such as the proteins of the rhinovirus, etc.). By virtue of the ability of ICAM-2 to interact with members of the CD-18 family of glycoproteins, it may be used to suppress (i.e. to prevent, or attenuate) inflammation.

The term "inflammation," as used herein, is meant to include both the reactions of the specific defense system, and the reactions of the non-specific defense system.

As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, delayed type hypersensitivity response mediated by T-cells (as seen, for example in individuals who test "positive" in the Mantaux test), etc. Chronic inflammatory diseases and the rejection of transplanted tissue and organs are further examples of inflammatory reactions of the specific defense system.

As used herein, a reaction of the "non-specific defense system" is intended to refer to a reaction mediated by leukocytes incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative coliris; Crohn's disease; necrotizing enterocolitis; granulocyte transfusion associated syndromes; and cytokine-induced toxicity.

As discussed above, the binding of ICAM-2 molecules to the members of CD-18 family of molecules is of central importance in cellular adhesion. Through the process of adhesion, lymphocytes are capable of continually monitoring an animal for the presence of foreign antigens. Although these processes are normally desirable, they are also the cause of organ transplant rejection, tissue graft rejection and many autoimmune diseases. Hence, any means capable of attenuating or inhibiting cellular adhesion would be highly desirable in recipients of organ transplants (especially kidney transplants), tissue grafts, or for autoimmune patients.

Monoclonal antibodies to members of the CD-18 family inhibit many adhesion dependent functions of leukocytes including binding to endothelium (Haskard, D. et al., *J. Immunol.* 137:2901–2906 (1986)), homotypic adhesions (Rothlein, R. et al., *J. Exp. Med.* 163:1132–1149 (1986)), antigen and mitogen induced proliferation of lymphocytes (Davignon, D. et al., *Proc. Natl. Acad. Sci., USA* 78:4535–4539 (1981)), antibody formation (Fischer, A. et al., *J. Immunol.* 136:3198–3203 (1986)), and effector functions of all leukocytes such as lytic activity of cytotoxic T cells (Krensky, A. M. et al., *J. Immunol.* 132:2180–2182 (1984)), macrophages (Strassman, G. et al., *J. Immunol.* 36:4328–4333 (1986)), and all cells involved in antibody-dependent cellular cytotoxicity reactions (Kohl, S. et al., *J. Immunol.* 133:2972–2978 (1984)). In all of the above functions, the antibodies inhibit the ability of the leukocyte to adhere to the appropriate cellular substrate which in turn inhibits the final outcome. Such functions, to the extent that they involve ICAM-2/LFA-1 interactions, can be suppressed with anti-ICAM-2 antibody.

Thus, monoclonal antibodies capable of binding to ICAM-2 can be employed as anti-inflammatory agents in a mammalian subject. Significantly, such agents differ from general anti-inflammatory agents in that they are capable of selectively inhibiting adhesion, and do not offer other side effects such as nephrotoxicity which are found with conventional agents.

Since ICAM-2, particularly in soluble form is capable of acting in the same manner as an antibody to members of the CD-18 family, it may be used to suppress inflammation. Moreover, the functional derivatives and antagonists of ICAM-2 may also be employed to suppress inflammation.

1. Suppressors of Delayed Type Hypersensitivity Reactions

ICAM-2 molecules mediate, in part, adhesion events necessary to mount inflammatory reactions such as delayed type hypersensitivity reactions. Thus, antibodies (especially monoclonal antibodies) capable of binding to ICAM-2 molecules have therapeutic potential in the attenuation or elimination of such reactions.

Alternatively, since ICAM-2 is an antagonist of the ICAM-1/LFA-1 interaction, ICAM-2 (particularly in solublilized form), or its functional derivatives can be used to suppress delayed type hypersensitivity reactions.

These potential therapeutic uses may be exploited in either of two manners. First, a composition containing a monoclonal antibody against ICAM-2 may be administered to a patient experiencing delayed type hypersensitivity reactions. For example, Such compositions might be provided to a individual who had been in contact with antigens such as poison ivy, poison oak, etc. In the second embodiment, the monoclonal antibody capable of binding to ICAM-2 is administered to a patient in conjunction with an antigen in order to prevent a subsequent inflammatory reaction. Thus, the additional administration of an antigen with an ICAM-2-binding monoclonal antibody may temporarily tolerize an individual to subsequent presentation of that antigen.

2. Therapy for Chronic Inflammatory Disease

Since LAD patients that lack LFA-1 do not mount an inflammatory response, it is believed that antagonism of LFA-1's natural ligand, ICAM-2, will also inhibit an inflammatory response. The ability of antibodies against ICAM-2 to inhibit inflammation provides the basis for their therapeutic use in the treatment of chronic inflammatory diseases and autoimmune diseases such as lupus erythematosus, autoimmune thyroiditis, experimental allergic encephalomyelitis (EAE), multiple sclerosis, some forms of diabetes, Reynaud's syndrome, rheumatoid arthritis, etc. Such antibodies may also be employed as a therapy in the treatment of psoriasis. In general, the monoclonal antibodies capable of binding to ICAM-2 may be employed in the treatment of those diseases currently treatable through steroid therapy.

In accordance with the present invention, such inflammatory and immune rejection responses may be suppressed (i.e. either prevented or attenuated) by providing to a subject in need of such treatment an amount of an anti-inflammatory agent sufficient to suppress said inflammation. Suitable anti-inflammatory agents include: an antibody capable of binding to ICAM-2; a fragment of an antibody, which fragment is capable of binding to ICAM-2; ICAM-2; a functional derivative of ICAM-2; a non-immunoglobulin antagonist of ICAM-2 other than ICAM-1 or a non-immunoglobulin antagonist of ICAM-2 other than LFA-1. Especially preferred are anti-inflammatory agents composed of a soluble functional derivative of ICAM-2. Such anti-inflammatory treatment can also include the additional administration of an agent selected from the group consisting of: an antibody capable of binding to LFA-1; a functional derivative of an antibody, said functional derivative being capable of binding to LFA-1; and a non-immunoglobulin antagonist of LFA-1.

The invention further includes the above-described methods for suppressing an inflammatory response of the specific defense system in which an immunosuppressive agent is additionally provided to the subject. Such an agent is preferably provided at a dose lower (i.e. a "sub-optimal" dose) than that at which it would normally be required. The use of a sub-optimal dose is possible because of the synergistic effect of the agents of the present invention. Examples of suitable immunosuppressive agents include dexamethesone, azathioprine, ICAM-1, cyclosporin A, etc.

3. Therapy for Non-Specific Inflammation

The present invention derives in part from the discovery that granulocyte-endothelial cell adherence results from the interaction of glycoproteins of the CD-18 family with the endothelium. Since cellular adhesion is required in order that leukocytes may migrate to sites of inflammation and/or carry out various effector functions contributing to inflammation, agents which inhibit cellular adhesion will attenuate or prevent such inflammation. Such inflammatory reactions are due to reactions of the "non-specific defense system" which are mediated by leukocytes incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity.

The anti-inflammatory agents of the present invention are compounds capable of specifically antagonizing the interaction of the CD-18 complex on granulocytes with endothelial cells. Such antagonists comprise: ICAM-2; a functional derivative of ICAM-2; and a non-immunoglobulin antagonist of ICAM-2 other than ICAM-1, or a member of the CD-18 family of molecules.

B. Suppressors of Organ and Tissue Rejection

Since ICAM-2, particularly in soluble form is capable of acting in the same manner as an antibody to members of the CD-18 family, it may be used to suppress organ or tissue rejection caused by any of the cellular adhesion-dependent functions. Moreover, anti-ICAM-2 antibody and the functional derivatives and antagonists of ICAM-2 may also be employed to suppress such rejection.

ICAM-2 and antibodies capable of binding to ICAM-2 can be used to prevent organ or tissue rejection, or modify autoimmune responses without the fear of such side effects, in the mammalian subject.

Importantly, the use of monoclonal antibodies capable of recognizing ICAM-2 may permit one to perform organ transplants even between individuals having HLA mismatch.

C. Adjunct to the Introduction of Antigenic Material Administered for Therapeutic or Diagnostic Purposes Immune responses to therapeutic or diagnostic agents such as, for example, bovine insulin, interferon, tissue-type plasminogen activator or murine monoclonal antibodies substantially impair the therapeutic or diagnostic value of such agents, and can, in fact, causes diseases such as serum sickness. Such a situation can be remedied through the use of the antibodies of the present invention. In this embodiment, such antibodies would be administered in combination with the therapeutic or diagnostic agent. The addition of the antibodies prevents the recipient from recognizing the agent, and therefore prevents the recipient from initiating an immune response against it. The absence of such an immune response results in the ability of the patient to receive additional administrations of the therapeutic or diagnostic agent.

ICAM-2 (particularly in solubilized form) or its functional derivatives may be employed interchangeably with ICAM-1, or with antibodies capable of binding to LFA-1 in the treatment of disease. Thus, in solubilized form, such molecules may be employed to inhibit organ or graft rejection. ICAM-2, or its functional derivatives may be used in the same manner as anti-ICAM-2 antibodies to decrease the immunogenicity of therapeutic or diagnostic agents.

D. Suppressors of Tumor Metastasis

The agents of the present invention may also be employed to suppress the metastasis of a hematopoietic tumor cell, which requires a functional member of the CD-18 family for migration. In accordance with this embodiment of the present invention, a patient in need of such treatment is provided with an amount of an agent (such as an antibody capable of binding to ICAM-2; a toxin-derivatized antibody capable of binding to ICAM-2; a fragment of an antibody, the fragment being capable of binding to ICAM-2; a toxin-derivatized fragment of an antibody, the fragment being capable of binding to ICAM-2; ICAM-2; a functional derivative of ICAM-2; and a non-immunoglobulin antagonist of ICAM-2 other than ICAM-1) sufficient to suppress said metastasis.

The invention also provides a method of suppressing the growth of an ICAM-2-expressing tumor cell which comprises providing to a patient in need of such treatment an amount of an agent sufficient to suppress said growth. Suitable agents include an antibody capable of binding to ICAM-2; a toxin-derivatized antibody capable of binding to ICAM-2; a fragment of an antibody, the fragment being capable of binding to ICAM-2; a toxin-derivatized fragment of an antibody, the fragment being capable of binding to ICAM-2; ICAM-2; a functional derivative of ICAM-2; a non-immunoglobulin antagonist of ICAM-2 other than ICAM-1; a toxin-derivatized member of the CD-18 family of molecules; and a toxin-derivatized functional derivative of a member of the CD-18 family of molecules.

The invention also provides a method of suppressing the growth of an LFA-1-expressing tumor cell which comprises providing to a patient in need of such treatment an amount of a toxin sufficient to suppress said growth. Suitable toxins include a toxin-derivatized ICAM-2, or a toxin-derivatized functional derivative of ICAM-2.

E. Suppressors of Viral Infection

ICAM-1 has recently been shown to be subverted as a receptor by the major group of rhinoviruses (Greve, J. M. et al., *Cell* 56:839–847 (1989); Staunton, D. E. et al., *Cell* 56:849–853 (1989); Tomassini, J. E. et al., *Proc. Natl. Acad. Sci. (U.S.A.)* 86:4907–4911 (1989), which references are incorporated herein by reference). Rhinoviruses, members of the small, RNA-containing, protein-encapsidated picornavirus family, cause 40–50% of common colds (Rueckert, R. R., In: *Fields Virology,* Fields, B. N. et al. (eds.), Raven Press, N.Y., (1985) pp 705–728; Sperber, S. J. et al. *Antimicr. Aqents Chemo.* 32:409–419 (1988), which references are incorporated herein by reference). Over 100 immunologically non-crossreactive rhinoviruses have been defined, of which 90% bind to ICAM-1.

Besides ICAM-1, the cell adhesion molecule CD4 and the complement receptor-CR2 have recently been found to be subverted as virus receptors by HIV and EBV viruses, respectively (Maddon, P. J., *Cell* 47:333–348 (1986); Fingeroth, J. D., et al., *Proc, Natl. Acad. Sci. USA* 81:4510–4514 (1984), which references are incorporated herein by reference). Further, a molecule with an Ig domain structure similar to ICAM-1 and which may function in cellular adhesion is a polio virus receptor (Mendelsohn, C. L., et al., *Cell.* 56:855–865 (1989)).

ICAM-2 and its functional derivatives may act as receptors for viral (particularly by rhinoviruses, and particularly rhinoviruses of the minor serotype) attachment or infection. Thus, antibody to ICAM-2 (or fragments thereof), ICAM-2, or functional derivatives of ICAM-2, may be employed to block such attachment or infection, and to thereby suppress viral infection.

F. Diagnostic and Prognostic Applications

Monoclonal antibodies capable of binding to ICAM-2 may be employed as a means of imaging or visualizing the sites of ICAM-2 expression and inflammation in a patient. In such a use, the monoclonal antibodies are detectably labeled, through the use of radioisotopes, affinity labels (such as biotin, avidin, etc.) fluorescent labels, paramagnetic atoms, labeled anti-ICAM-2 antibody, etc. Procedures for accomplishing such labeling are well known to the art. Clinical application of antibodies in diagnostic imaging are reviewed by Grossman, H. B., *Urol. Clin. North Amer.* 13:465–474 (1986)), Unger, E. C. et al., *Invest. Radiol.* 20:693–700 (1985)), and Khaw, B. A. et al., *Science* 209:295–297 (1980)).

The presence of ICAM-2 expression may also be detected through the use of binding ligands, such as mRNA, cDNA, or DNA which bind to ICAM-2 gene sequences, or to ICAM-2 mRNA sequences, of cells which express ICAM-2. Techniques for performing such hybridization assays are described by Maniatis, T. et al., In: *Molecular Clonincl, a Laboratory Manual,* Coldspring Harbor, N.Y. (1982), and by Hayroes, B. D. et al., In: *Nucleic Acid Hybrization, a Practical Approach,* IRL Press, Washington, D.C. (1985), which references are herein incorporated by reference.

The detection of loci of such detectably labeled antibodies is indicative of a site of ICAM-2 expression or tumor development. In one embodiment, this examination for expression is done by removing samples of tissue or blood and incubating such samples in the presence of antibodies which are or which can be detectably labeled. In a preferred embodiment, this technique is done in a non-invasive manner through the use of magnetic imaging, fluorography, etc. Such a diagnostic test may be employed in monitoring organ transplant recipients for early signs of potential tissue rejection. Such assays may also be conducted in efforts to determine an individual's predilection to rheumatoid arthritis or other chronic inflammatory diseases.

For example, by radioactively labeling the antibodies or antibody fragments, it is possible to detect the antigen through the use of radioimmune assays. A good description of a radioimmune assay (RIA) may be found in *Laboratory Techniques and Biochemistry in Molecular Biology,* by Work, T. S., et al., North Holland Publishing Company, N.Y. (1978), with particular reference to the chapter entitled "An Introduction to Radioimmune Assay and Related Techniques" by Chard, T., incorporated by reference herein. Alternatively, flouresecent, enzyme, or other suitable labels can be employed.

Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}H$, $^{111}In$, $^{125}I$, $^{131}I$, $^{32}P$, $^{35}S$, $^{14}C$, $^{51}Cr$, $^{57}Co$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. Examples of suitable non-radioactive isotopic labels include $^{157}Gd$, $^{55}Mn$, $^{162}Dy$, $^{52}Tr$, $^{56}Fe$, etc.

Examples of suitable fluorescent labels include an $^{152}Eu$ label, a fluorescein label, a rhodamine label, a phycoerythrin label, a phycocyanin label, an allophycocyanin label, an o-phthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

VI. ADMINISTRATION OF THE COMPOSITIONS OF THE PRESENT INVENTION

The therapeutic effects of ICAM-2 may be obtained by providing to a patient the entire ICAM-2 molecule, or any therapeutically active peptide fragments thereof. Of special interest are therapeutically active peptide fragments of ICAM-2 which are soluble.

ICAM-2 and its functional derivatives may be obtained either synthetically, through the use of recombinant DNA technology, or by proteolysis, or by a combination of such methods. The therapeutic advantages of ICAM-2 may be augmented through the use of functional derivatives of ICAM-2 possessing additional amino acid residues added to enhance coupling to carrier or to enhance the activity of the ICAM-2. The scope of the present invention is further intended to include functional derivatives of ICAM-2 which lack certain amino acid residues, or which contain altered amino acid residues, so long as such derivatives posess or affect a biological or pharmacological activity of ICAM-2.

Both the antibodies of the present invention and the ICAM-2 molecule disclosed herein are said to be "substantially free of natural contaminants" if preparations which contain them are substantially free of materials with which these products are normally and naturally found.

The present invention extends to antibodies, and biologically active fragments thereof, (whether polyclonal or monoclonal) which are capable of binding to ICAM-2. Such antibodies may be produced either by an animal, or by tissue culture, or recombinant DNA means.

In providing a patient with antibodies, or fragments thereof, capable of binding to ICAM-2, or when providing ICAM-2 (or a fragment, variant, or derivative thereof) to a recipient patient, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg to 10 mg/kg (body weight of patient), although a lower or higher dosage may be administered. When providing ICAM-2 molecules or their functional derivatives to a patient, it is preferable to administer such molecules in a dosage which also ranges from about 1 pg/kg to 10 mg/kg (body weight of patient) although a lower or higher dosage may also be administered. As discussed below, the therapeutically effective dose can be lowered if the anti-ICAM-2 antibody is additionally administered with an anti-LFA-1 antibody. As used herein, one compound is said to be additionally administered with a second compound when the administration of the two compounds is in such proximity of time that both compounds can be detected at the same time in the patient's serum.

Both the antibody capable of binding to ICAM-2 and ICAM-2 itself may be administered to patients intravenously, intramuscularly, subcutaneously, enterally, or parenterally. When administering antibody or ICAM-2 by injection, the administration may be by continuous infusion, or by single or multiple boluses.

The agents of the present invention are intended to be provided to recipient subjects in an amount sufficient to suppress inflammation. An amount is said to be sufficient to "suppress" inflammation if the dosage, route of administration, etc. of the agent are sufficient to attenuate or prevent inflammation.

Anti-ICAM-2 antibody, or a fragment thereof, may be administered either alone or in combination with one or more additional immunosuppressive agents (especially to a recipient of an organ or tissue transplant). The administration of such compound(s) may be for either a "prophylactic" or "therapeutic" purpose. When provided prophylactically, the immunosuppressive compound(s) are provided in advance of any inflammatory response or symptom (for example, prior to, at, or shortly after) the time of an organ or tissue transplant but in advance of any symptoms of organ rejection). The prophylactic administration of the compound(s) serves to prevent or attenuate any subsequent inflammatory response (such as, for example, rejection of a transplanted organ or tissue, etc.). When provided therapeutically, the immunosuppressive compound(s) is provided at (or shortly after) the onset of a symptom of actual inflammation (such as, for example, organ or tissue rejection). The therapeutic administration of the compound(s) serves to attenuate any actual inflammation (such as, for example, the rejection of a transplanted organ or tissue).

The anti-inflammatory agents of the present invention may, thus, be provided either prior to the onset of inflammation (so as to suppress an anticipated inflammation) or after the initiation of inflammation.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The antibody and ICAM-2 molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human-serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of anti-ICAM-2 antibody or ICAM-2 molecule, or their functional derivatives, together with a suitable amount of carrier vehicle.

Additional pharmaceutical methods may be employed to control the duration of action. Control release preparations may be achieved through the use of polymers to complex or absorb anti-ICAM-2 antibody or ICAM-2, or their functional derivatives. The controlled delivery may be exercised by selecting appropriate macromolecules (for example polyesters, polyamino acids, polyvinyl, pyrrol idone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-ICAM-2 antibody or ICAM-2 molecules, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethyacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The invention further includes a pharmaceutical composition comprising: (a) an anti-inflammatory agent (such as an antibody capable of binding to ICAM-2; a fragment of an antibody, said fragment being capable of binding to ICAM-2; ICAM-2; a functional derivative of ICAM-2; and a non-immunoglobulin antagonist of ICAM-2 other than ICAM-1, and (b) at least one immunosuppressive agent. Examples of suitable immunosuppressive agents include: dexamethesone, azathioprine and cyclosporin A.

Having now generally described the invention, the same will be more readily understood through reference to the following examples which are provided by way of illustration, and are not intended to be limiting of the present invention, unless specified.

EXAMPLE 1

CLONING OF ICAM-2 cDNA

In order to clone cDNA capable of encoding ICAM-2, a modification of the procedure of Aruffo and Seed (Seed, B. et al., *Proc. Natl. Acad. Sci. USA* 84:3365–3369 (1987)) for selecting cDNAs by expression in COS cells was employed to pan for ligand-bearing COS cells on functionally-active, purified LFA-1 bound to plastic Petri dishes.

In detail, LFA-1 was purified from SKW-3 lysate by immunoaffinity chromatography on TS2/4 LFA-1 MAb Sapharose and eluted at pH 11.5 in the presence of 2 mM $MgCl_2$ and 1% octylglucoside. LFA-1 (10 µg/200 µl/6 cm plate) was bound to bacteriological Petri dishes by diluting octylglucoside to 0.1% in PBS with 2 mM $MgCl_2$ and overnight incubation at 4° C. Plates were blocked with 1% BSA and stored in PBS/2mM $MgCl_2$/0.2% BSA/0.025% azide/50 µg/ml gentamycin.

Synthesis of a cDNA library from LPS-stimulated umbilical vein endothelial cells by the method of Gubler and Hoffman was performed as described by Staunton et al. (Staunton, D. E. et al., *Cell* 52:925–933 (1988)). Following second strand. synthesis the cDNA was ligated to Bst X1 adaptors (Seed, B. et al., *Proc. Natl. Acad. Sci. USA* 84:3365–3369 (1987)) and cDNA's >600 bp were selected by low melting point (LMP) agarose gel electrophoresis. The cDNA was then ligated to CDM8 (Seed, B., *Nature* 329:840–842 (1987)), introduced into *E. coli* host MC1061/P3 and plated to obtain $5 \times 10^5$ colonies. The colonies were suspended in LB medium, pooled and plasmid prepared by standard alkali lysis method (Maniatis, T. et al., in *Molecular Cloning: A Laboratory Manual*, Cold Spring Harbor Laboratory (1982)). Ten 10 cm plates of COS cells at 50% confluency were transfected with 10 µg/plate of the plasmid cDNA library using DEAE-dextran (Kingston, R. E., in *Curent Protocols in Molecular Biology*, 9.0.1–9.9.6, Greene Publishing Associates (1987)). ICAM-2 is trypsin-resistant on endothelial and SKW-3 cells. COS cells three days post transfection were suspended by treatment with 0.025% trypsin/1 mM EDTA/HBSS (Gibco) and panned (Seed, B. et al., *Proc. Natl. Acad. Sci. USA* 84:3365–3369 (1987)) on LFA-1 coated plates as described below for $^{51}$Cr-labelled COS cells. Adherent cells were released by addition of EDTA to 10 mM.

Plasmid was recovered from the adherent population of COS cells in Hirt supernatants (Hirt, B. j., *J. Mol. Biol.* 26:365–369 (1967)). The *E. coli* strain MC1061/P3 was then transformed with the plasmid, colonies on plates were suspended in LB medium, pooled and plasmid prepared by alkali-lysis method. Selection of LFA-1-adherent transfected COS cells and plasmid recovery was repeated for two more cycles. Pooled colonies obtained after the third cycle were grown to saturation in 100 ml of LB medium with 18 µg/ml tetracycline and 20 µg/ml ampicillin. Plasmid was prepared and fractionated by 1% LMP-agarose gel electrophoresis and MC1061/p3 was transformed separately with plasmid from nine different size fractions. Individual plasmids from the fraction with greatest activity in promoting COS cell adhesion to LFA-1 were examined for insert size by digestion with Xba1 and tested in the COS cell adherence assay. This yielded one plasmid with an ICAM-2 cDNA insert of 1.1 kb, pCDIC2.27.

For adhesion assays, the ICAM-2 plasmid pCDIC2.27 or an ICAM-1 construct containing the 1.8 kb SalI, KpnI fragment (Staunton, D. E. et al., *Cell* 52:925–933 (1988)) in CDM8 (2 µg/10 cm plate) were introduced into COS cells using DEAE-Dextran. COS cells were suspended with 0.025% trypsin/1 mM EDTA/HBSS three days post transfection and labelled with $^{51}$Cr. Approximately $2 \times 10^5$ $^{51}$Cr labelled COS cells in 2 ml PBS/5% FCS/2 mM $MgCl_2$/0.025% azide (buffer) with 5 µg/ml of the MAb indicated were incubated in LFA-1-coated 6 cm plates at 25° C. for 1 hour. Non-adherent cells were removed by gentle rocking and three washes with buffer. Adherent cells were eluted by the addition of EDTA to 10 mM and γ-counted.

The feasibility of this procedure was demonstrated using COS cells transfected with the previously cloned ICAM-1 cDNA (FIG. 1A). ICAM-1 was expressed on 25% of the transfected COS cells. After panning, nonadherent cells were depleted of ICAM-1$^+$ cells, whereas adherent cells released from LFA-1-coated plastic by EDTA were almost completely ICAM-1$^+$. Adherence of ICAM-1$^+$ cells to LFA-1-coated plastic was inhibited with RR1/1 ICAM-1 MAb. LFA-1-coated on Petri dishes was stable to >5 cycles of COS cell adherence and elution with EDTA; plates were stored with $Mg^{2+}$ at 4° C. in between use.

To clone ICAM-2, a cDNA library in the plasmid vector CDM8 was prepared from endothelial cells, which demonstrate both the ICAM-1-dependent and ICAM-1-independent components of LFA-1-dependent adhesion (Dustin, M. L. et al., *J. Cell. Biol.* 107:321–331 (1988)). Transfected COS cells were incubated in LFA-1-coated petri dishes with ICAM-1 MAb present to prevent isolation of ICAM-1 cDNA's. Adherent cells were eluted with EDTA and plasmids were isolated and amplified in *E. coli*. Following three cycles of transfection, adherence, and plasmid isolation; and one size fractionation, 30 plasmids were analyzed by restriction endonuclease digestion. Of three with inserts >1.0 kb, one plasmid introduced into COS cells by transfection yielded adherence to LFA-1.

Figure 1B:
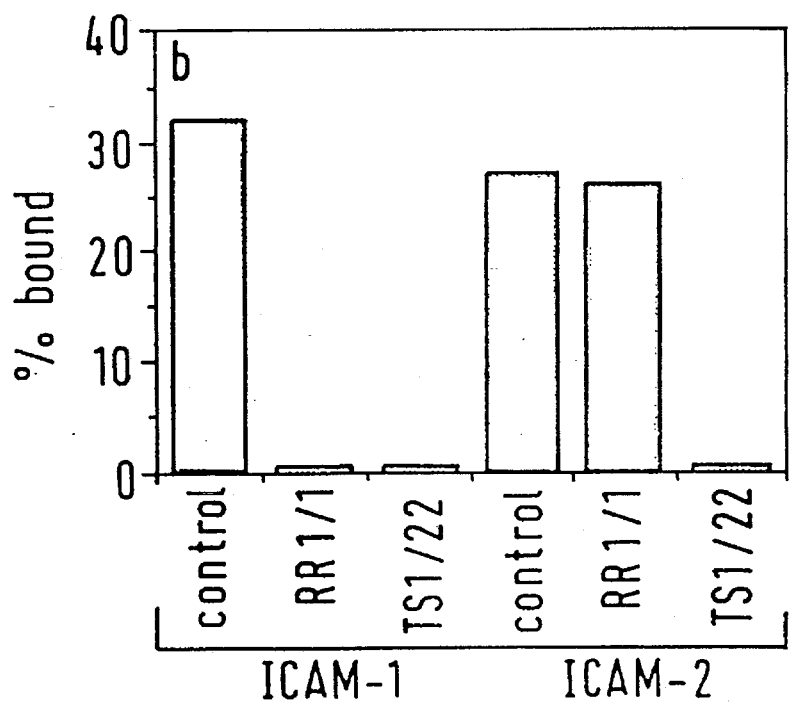

The isolated plasmid conferred adherence to LFA-1 on a high percentage of the transfected cells, similar to the percentage seen with ICAM-1 transfection (FIG. 1B). Adherence was blocked by LFA-1 mAb, but in contrast to ICAM-1 transfectants, not by ICAM-1 mAb (FIG. 1B). Futhermore, cells transfected with this plasmid did not react with a panel of four ICAM-1 mAb. Thus, all functional criteria for a cDNA encoding a second LFA-1 ligand were fulfilled, and the ligand was designated "ICAM-2."

EXAMPLE 2

CHARACTERIZATION OF ICAM-2 cDNA SEQUENCE

The ICAM-2 cDNA sequence of 1052 bp (FIG. 2) contains a 62 bp 5' and a 167 bp 3' untranslated region. An AATACA polyadenylation signal at position 1019, which in contrast to AATAAA, occurs in approximately 2% of vertebrate mRNAs (Wickens, M. et al., *Science* 226:1045–1051 (1984)), is followed at 1058 bp by a poly(A) tail. The longest open reading frame begins with the first ATG at position 63 and ends with a TAG termination codon at position 885. Hydrophobicity analysis (Kyte, J. et al., *J. Mol. Biol.* 157:105–132 (1982)) and usage of amino acids around cleavage sites (von Heijne, G., *Nucleic Acids Research* 14:4683–4690 (1986)) predict a 21 residue signal peptide (FIG. 2).

The predicted mature sequence contains from amino acid 1 to 201 a putative extracellular domain followed by a 26 residue hydrophobic putative transmembrane domain and a 26 residue cytoplasmic domain. Four turns of the putatively e-helical transmembrane segment are amphipathic, with threonine and serine residues falling on one side, suggesting the possibility of self-association or association with other membrane proteins in the plane of the membrane. The cytoplasmic domain is unusually basic, and in contrast to most cytoplasmic domains which are hydrophilic, is of average hydrophobicity. The predicted mass of the mature polypeptide is 28,176 daltons which, if the six predicted N-linked glycosylation sites are used, would result in a ICAM-2 glycoprotein of approximately 46 Kd.

EXAMPLE 3

DNA AND RNA HYBRIDIZATION ANALYSES

The isolated ICAM-2 cDNA clones were analyzed using both Northern and Southern hybridization. Northern blots used 6 μg of poly(A)$^+$ RNA which was denatured and electrophoresed through a 1% agarose-formaldehyde gel (Maniatis, T. et al., in *Molecular Cloning: A Laboratory Manual*, Cold Spring Harbor Laboratory (1982)) and electrotransferred to a nylon membrane (Zeta Probe, BioRad). Completion of transfer was confirmed by UV trans-illumination of the gel and fluorescent photography of the blot.

The genomic DNAs were digested with five times the manufacturer's recommended quantity of EcoRI and HindIII endonucleases (New England Biolabs). Following electrophoresis through a 0.8% agarose gel, the DNAs were transferred to Zeta Probe. RNA and DNA blots were prehybridized and hybridized following standard procedures (Maniatis, T. et al., in *Molecular Cloning: A Laboratory Manual*, Cold Spring Harbor Laboratory (1982)) using ICAM-2 or ICAM-1 cDNAs labeled with α[$^{32}$P]d XTP's by random priming (Boehringer Mannheim).

The 1.1 kb ICAM-2 cDNA hybridizes to a 1.4 kb poly(A)$^+$ mRNA and weakly to a 3 kb mRNA (FIG. 3A), distinct from the 3.3 kb and 2.4 kb ICAM-1 mRNA (FIG. 3B). mRNA was examined in cells which have been characterized functionally for ICAM-1-dependent and second ligand-dependent binding to LFA-1. ICAM-1 mRNA is strongly induced in endothelial cells by LPS (FIG. 3B, lanes 2 and 3). In contrast, ICAM-2 mRNA is strongly expressed basally in endothelial cells and is not induced further by LPS (FIG. 3A, lanes 2 and 3). This correlates with strong basal and non-inducible expression of the LFA-1-dependent, ICAM-1-independent pathway in endothelial cells and inducibility of the ICAM-1-dependent pathway (Dustin, M. L. et al., *J. Cell. Biol.* 107:321–331 (1988)).

ICAM-2 mRNA is present in a wide variety of cell types including Ramos and BBN B lymphoblastoid, U937 monocytic, and SKW3 lymphoblastoid cell lines (FIG. 3A, lanes 1,4,6, and 8), as shown by moderate or long autoradiogram exposure. Of these, SKW3, U937, and BBN have been shown to exhibit LFA-1-dependent, ICAM-1-independent adhesion to LFA-1$^+$ cells (Rothlein, R. et. al., *J. Immunol.* 137:1270–1274 (1986); Makgoba, M. W. et al., *Eur. J. Immunol.* 18:637–640 (1988)), and to LFA-1-coated plastic. The HeLa epithelial cell line, which exhibits only the ICAM-1-dependent component of LFA-1-dependent adhesion (Makgoba, M. W. et al., *Eur. J. Immunol.* 18:637–640 (1988)), shows no ICAM-2 mRNA (FIG. 3A, lane 5), even after prolonged autoradiogram exposure. The cell distribution of ICAM-2 is thus consistent with the ICAM-1-independent component of LFA-1-dependent adhesion.

Southern blots of genomic DNA (FIG. 3D) hybridized with the ICAM-2 cDNA showed a single predominant EcoRI fragment of 8.2 kb and HindIII fragment of 14 kb, suggesting a single gene with most of the coding information present in 8 kb.

EXAMPLE 4

COMPARISON OF THE AMINO ACID SEQUENCES OF ICAM-1 AND ICAN-2

Because of their functional similarity as LFA-1 ligands, the amino acid sequences of ICAM-2 and ICAM-1 were compared. ICAM-1 is a member of the Ig superfamily and its extracellular domain consists entirely of five C-like domains. The 201 amino acid extracellular domain of ICAM-2 consists of 2 Ig C-like domains, with putative intradomain disulfide-bonded cysteines spaced 43 and 56 residues apart and a predicted β strand structure (FIG. 4). Remarkably, the two Ig-like domains of ICAM-2 are 34% identical in amino acid sequence to the two most N-terminal Ig-like domains of ICAM-1 (FIG. 4), with an ALIGN score 15 s.d. above the mean, and 27% identical to ICAM-1 domains 3 and 4, with an ALIGN score 3 s.d. above the mean.

Search of the NBRF and SWISS-PROT protein databases yielded only partial domain homologies with other members of the Ig superfamily, primarily with HLA Class II antigens. ICAM-2 shows somewhat fewer conserved residues characteristic of Ig domains than ICAM-1. ICAM-2 is 17% and 19% identical to the two N-terminal domains of the adhesion molecules NCAM (Cunningham, B. A. et al., *Science* 236:799–806 (1987)) and MAG (Salzer, J. L. et al., *J. Cell Biol.* 104:957–965 (1987)), respectively, while ICAM-1 is 19% and 20% identical, respectively.

Lymphocyte function associated antigen-1 (LFA-1) and intercellular adhesion molecule-1 (ICAM-1) were identified by selecting MAb which blocked T lymphocyte-mediated killing, and homotypic adhesion, respectively (Rothlein, R. et al., *J. Immunol.* 137:1270–1274 (1986); Davignon, D. et al., *Proc. Natl. Acad. Sci. USA* 78:4535–4539 (1981)). In contrast, ICAM-2 has been defined using a functional cDNA selection procedure which requires no previous identification of the protein by biochemical or immunological techniques.

Isolation of a cDNA for ICAM-2 confirms the postulated existence of an alternative LFA-1 ligand. The distribution of mRNA for ICAM-2 on a limited number of cells which have been characterized for ICAM-1-dependent and ICAM-1-independent adhesion to LFA-1 suggests that ICAM-2 could account for all of the observed ICAM-1-independent LFA-1-dependent adhesion.

ICAM-2 and the two N-terminal domains of ICAM-1 are much more like one another than like other members of the Ig superfamily, demonstrating a subfamily of Ig-like molecules which bind to LFA-1. Significantly, the LFA-1-binding region of ICAM-1 has been mapped to domains 1 and 2 by domain deletion and systematic amino acid substitution. Thus, there is both structural and functional homology. ICAM-2 is the second example of an Ig-family member which binds to an integrin. Although there is little precedence among cell adhesion receptors, among the integrins a number of receptors for extracellular matrix components have been shown to recognize multiple ligands (Hynes, R. O., *Cell* 48:549–554 (1987); Ruoslahti, E. et al., *Science* 238:491–497 (1987)).

Neither ICAM-1 or ICAM-2 contains an RGD sequence, and thus the mode of recognition by LFA-1 may differ from integrins which bind extracellular matrix components (Hynes, R. O., *Cell* 48:549–554 (1987); Ruoslahti, E. et al., *Science* 238:491–497 (1987)). The cellular ligands recognized by Mac-1 and p150,95, leukocyte integrins closely related to LFA-1, may belong to the same Ig subfamily. ICAM-1 has recently been demonstrated to be a receptor for the major group of rhinoviruses which cause 50% of common colds. ICAM-2 may also function as a receptor for rhinoviruses or other picornaviruses. Thus, it may be used in a therapy to suppress (i.e. prevent or attenuate) infection from such viruses.

A family of ligands for LFA-1 emphasizes the importance of this recognition pathway and may be a mechanism for imparting fine specificity and functional diversity. A number of differences between ICAM-1 and ICAM-2 are of potential importance. ICAM-1 is inducible on most cells while ICAM-2 expression is not affected by cytokines on the cells thus far tested. The three additional domains on ICAM-1 are expected to project its LFA-1 binding site further from the cell surface than that of ICAM-2, suggesting that closer cell-cell contact would be required for LFA-1:ICAM-2 than LFA-1:ICAM-1 interaction. ICAM-2 transfected COS cells are more readily detached than ICAM-1 transfected COS cells from LFA-1 coated plastic as the washing shear force is increased. This may be due to the smaller size of ICAM-2 which may make it less accessible to LFA-1 on the artificial substrate, or to differences in sequence which impart differences in affinity.

The distinct cytoplasmic domains of ICAM-1 and ICAM-2 may impart different signals or may cause differing localization on the cell surface; likewise, signalling or interaction with the cytoskeleton by LFA-1 may differ depending on whether ICAM-1 or ICAM-2 is bound.

ICAM-1 and a second LFA-1 counter-receptor, ICAM-2, thus constitute a subfamily of the immunoglobulin (Ig) superfamily (Staunton, D. E., et al., *Cell* 52:925–933 (1988), which reference is incorporated herein by reference). ICAM-1 possesses five Ig-like C domains whereas ICAM-2 possesses two, which are most homologous to the amino terminal domains of ICAM-1. ICAM-1 and ICAM-2, expressed on a variety of cell types, support various leukocyte adhesion dependent functions including induction and effector functions in the immune response. ICAM-1 expression is highly inducible by cytokines and thus the LFA-1/ICAM-1 adhesion system is able to guide leukocyte migration and localization during inflammation (Rothlein, R. *J. Immunol.* 137:1270–1274 (1986); Marlin, S. D. et al., *Cell* 51:813–819 (1987); Kishimoto, T. K. et al., *Adv. Immunol.* 46:149–182 (1989); Dustin, M. L. et al., *Immunol. Today* 9:213–215 (1988), all of which references are incorporated herein by reference).

ICAM-1 residues which have been defined above as being important to LFA-1 binding are conserved in other ICAMs (Staunton, D. E., et al. *Nature* 339:61–64 (1989), which reference is incorporated herein by reference). Human ICAM-1 is 50% identical to murine ICAM-1 and 35% identical to human ICAM-2 (Staunton, D. E., et al. *Nature* 339:61–64 (1989). The residues that are most critical to LFA-1 binding, E34 and Q73, are conserved both in mouse ICAM-1 and in human ICAM-2. This is consistent with the ability of both mouse ICAM-1 and human ICAM-2 (Staunton, D. E., et al. *Nature* 339:61–64 (1989)) to bind to human LFA-1. One D2 N-linked glycosylation site at N156, which influences LFA-1 binding, is also conserved in ICAM-2. Several residues that are important to rhinovirus-14 binding, Q58, G46, D71, K77 and R166, are not conserved in mouse ICAM-1 or human ICAM-2 (Staunton, D. E. et al., *Cell* 56:849–853 (1989), which reference is incorporated herein by reference) which is consistent with the apparent inability of mouse cells (Colonno, R. J. et al., *J. Virol.* 57:7–12 (1986)) and ICAM-2 to bind rhinovirus-14.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated antibody which specifically binds to intercellular adhesion molecule-2, ICAM-2.

2. The antibody of claim 1, wherein said antibody blocks the binding of lymphocyte function-associated antigen-1 (LFA-1) to ICAM-2.

3. A fragment of the antibody of claim 1, wherein said fragment comprises the antigen binding site of said antibody and said fragment specifically binds to ICAM-2.

4. An isolated antibody which specifically binds to ICAM-2 further comprising a detectable label.

\* \* \* \* \*